United States Patent [19]
Balkus, Jr. et al.

[11] Patent Number: 5,122,363

[45] Date of Patent: Jun. 16, 1992

[54] ZEOLITE-ENCLOSED TRANSISTION AND RARE EARTH METAL IONS AS CONTRAST AGENTS FOR THE GASTROINTESTINAL TRACT

[75] Inventors: Kenneth J. Balkus, Jr., The Colony; A. Dean Sherry, Dallas, both of Tex.; Stuart W. Young, Portola Valley, Calif.

[73] Assignee: Board of Regents, The University of Texas System, Austin, Tex.

[21] Appl. No.: 624,106

[22] Filed: Dec. 7, 1990

[51] Int. Cl.$^5$ ............... G01N 31/00; G01N 24/00; C01B 33/24; A61K 33/06

[52] U.S. Cl. .................... 424/9; 424/1.1; 424/684; 424/4; 436/173; 514/836; 514/974; 423/328

[58] Field of Search ........... 424/9, 4, 1.1, 684; 436/173; 128/653 CA, 654, 653 R; 514/836, 974; 423/328

[56] References Cited

U.S. PATENT DOCUMENTS

| | | | |
|---|---|---|---|
| 4,388,285 | 6/1983 | Rankel et al. | 423/329 |
| 4,466,812 | 8/1984 | Takaishi et al. | 55/68 |
| 4,647,447 | 3/1987 | Gries et al. | 424/9 |
| 4,767,609 | 8/1988 | Stavrianpoulos | 424/1.1 |
| 4,774,957 | 4/1988 | Nambu et al. | 128/653 R |
| 4,797,267 | 1/1989 | Kuehl | 423/329 |

OTHER PUBLICATIONS

Ismatov et al. Chem. Abs. 103:114935J (1985).
Nemoshkalenko, W . et al. Chem. Abs. 103:27525G (1985).
Nesper, R. et al. Chem. Abs. 98:8704t (1983).
The Condensed Chemical Dictionary (1971) p. 190.
Atlas of Zeolite Structures (1987) p. 344.
Article in German by Claussen et al.. "Orale Kontrastmittel für die magnetische Resonanztomographie des Abdomens. Teil III: Erste Patientenuntersuchungen mit Gadolinium-DTPA", RöFo, vol. 148, p. 683, 1989, abstract only, article not translated.
Article by Braybrook and Hall, "Effect of pH on the Nuclear Magnetic Resonance Relaxivity of Encapsulated Solid Paramagnetic Substances", Drug Design and Delivery, vol. 4, pp. 93-95, 1989.
Article by Denkewicz, "Zeolite Science: An Overview", Journal of Materials Education, vol. 9, No. 5, pp. 519-564, 1987.
Article by Hahn et al., "First Clinical Trial of a New Superparamagnetic Iron Oxide for Use As an Oral Gastrointestinal Contrast Agent in MR Imaging", Radiology, vol. 175, pp. 695-700, 1990.

*Primary Examiner*—Glennon H. Hollrah
*Assistant Examiner*—Gary E. Hollinden
*Attorney, Agent, or Firm*—Arnold, White & Durkee

[57] ABSTRACT

The invention relates to a method of using zeolite enclosed paramagnetic ions as image brightening or image contrast agents. In particular, zeolite enclosed trivalent gadolinium is useful in MRI studies of the entire gastrointestinal tract, providing excellent images. Zeolite-enclosed gadolinium complexes may be conveniently administered in oral preparations without side effects of diarrhea. Other transition metal ions, including divalent manganese may be enclosed in any suitable zeolite which has ion exchange properties sufficient to exchange the selected metal.

27 Claims, 3 Drawing Sheets

ZEOLITE-ENCLOSED TRANSISTION AND RARE EARTH METAL IONS AS CONTRAST AGENTS FOR THE GASTROINTESTINAL TRACT

BACKGROUND OF THE INVENTION

1. Field of the Invention

The invention relates to contrast or imaging agents useful in vivo for studies and diagnosis of the gastrointestinal tract. The agents are zeolite materials enclosing a paramagnetic ion such as trivalent gadolinium. The loaded zeolites are particularly suitable for oral administration and function well as magnetic resonance imaging contrast or image brightening agents in the upper gastrointestinal tract.

2. Description of Related Art

The availability of sophisticated methods such as MRI and CT has contributed to the increased use of imaging technology in therapy and diagnostic studies. Gastrointestinal tract imaging is a particular area of interest because currently used imaging agents generally provide poor imaging, resulting in visualization of little more than gross blockages or anatomical abnormalities.

Barium sulfate and paramagnetic iron oxide are agents traditionally used for gastrointestinal studies. The latter material has become popular because of the paramagnetic properties of $Fe_2O_3$ which is suited for MRI studies, but it has many disadvantages. These include black bowel, side effects of diarrhea and, from an analytical standpoint most important, the presence of artifacts arising from clumping. When paramagnetic iron concentrates, it may become ferromagnetic, drastically altering its imaging properties. Even when images are obtained, the signal is black, making it difficult to distinguish imaged from nonimaged areas.

The development of imaging contrast agents, particularly for gastrointestinal tract studies has been slow. Historically, the most popular agent has been superparamagnetic iron oxide for magnetic imaging, due to its nonbiodegradability. Although good contrast effects have been achieved in some MR studies in the small bowel, increasing occurrence of blurring and 'metal' artifacts in the distal part of the bowel has been recorded (1). In other studies with superparamagnetic iron oxide, good resolution of the head and tail of the pancreas, anterior margins of the kidneys and para-aortic region has been shown in human patients. Some patients experienced episodes of diarrhea (2).

Magnetic imaging is particularly useful for the study and diagnosis of tumors or inflammatory abdominal diseases. Paramagnetic species represented by gadolinium seem to be potentially agents for these studies, the metal itself cannot be used in humans because of its toxic properties. Nevertheless, diethylenetriamine penta-acetic acid (DTPA) complexes of trivalent gadolinium have less toxicity than the uncomplexed salt and have been tested in human patients. Opacification of the gastrointestinal tract has been reported, but less than 60% of the magnetic resonance scans showed improved delineation of abdominal pathologies. Furthermore, nearly 40% of the patients reported diarrhea and meteorism (3).

Encapsulation of solid paramagnetic complexes in sulfonated ion-exchange resins for use in abdominal imaging has been suggested. It has been speculated that such encapsulation in acid-stable materials would prevent significant demetallation which otherwise occurs in the stomach when image contrasting agents are orally administered for gastrointestinal tract imaging (4).

Superparamagnetic iron oxide has been coated onto a polymer carrier matrix and evaluated as an oral contrast medium for MRI. Generally good images were obtained in the region of the small bowel, except the duodenum, but the useful concentration range appeared to be fairly narrow since some concentrations caused an artifact in the stomach after ingestion of the agent (I).

There is clearly a need for orally effective, well-tolerated agents that can be used in humans for imaging studies. In particular, an MRI imaging agent applicable to gastrointestinal tract studies would be useful for visualizing the anatomy of the intestinal tract and particularly to differentiate normal and pathological states, such as tumors. An effective, orally deliverable paramagnetic imaging contrast agent devoid of the common side effects currently encountered with the presently used GI imaging agents would represent a significant improvement over the iron and gadolinium complexes described. These compounds have several problems, including toxicity and lack of good image quality. Even with reports of improved compositions such as carrier complexes and matrices, some areas of the intestine are inadequately visualized with these materials and side effects still exist. For example, although trivalent gadolinium is an excellent paramagnetic MRI contrast species, its toxicity limits use in humans to its DTPA complex, which itself may exhibit toxicity.

A solution to many of the problems inherent in the use of presently used agents of choice in imaging the gastrointestinal tract has been discovered. A nontoxic zeolite carrier that preferentially binds paramagnetic metal ions within a lattice-like structure has been shown to have little toxicity and to exhibit excellent imaging properties. Furthermore, many of the problems associated with the use of superparamagnetic iron oxide are eliminated, including metal imaging and patient side effects such as diarrhea.

SUMMARY OF THE INVENTION

The present invention is a method of contrast imaging in humans or animals utilizing a zeolite-enclosed paramagnetic metal ion. The paramagnetic ion is preferentially bound by the zeolite. Preparations of paramagnetic metal ions enclosed in a zeolite are orally administrable and nontoxic. In a preferred embodiment, trivalent gadolinium is enclosed in CaA or NaX to form CaGdA or NaGdX.

Generally, the invention is an imaging method which involves administering a paramagnetic ion enclosed in zeolite. Most often the method will be used in humans but of course it could be used in animals, for example, in veterinary practice for diagnosis of gastrointestinal abnormalities. The amount of paramagnetic ion enclosed within the zeolite is enough to be effective as a contrast or imaging brightening agent. A particularly useful feature of this invention is the brightness of the areas imaged with zeolite enclosed paramagnetic ions. This contrasts with images obtained with superparamagnetic iron oxide which develop as dark or deep gray areas. Brightly imaged areas are preferred over dark contrast for visualizing the anatomy of the area and for detecting pathologies because delineation is increased.

Zeolite-enclosed paramagnetic ions are particularly useful for imaging studies in human beings and have many advantages over superparamagnetic iron oxide. Superparamagnetic iron tends to clump in the gastrointestinal tract causing a conversion from paramagnetic to ferromagnetic properties. Additionally, superparamagnetic iron oxide administered in the quantities necessary for satisfactory imaging causes unpleasant side effects in human beings, including diarrhea and meteorism. Such effects have not been observed with zeolite-enclosed trivalent gadolinium. The invention also overcomes the problems associated with toxicity of some of the paramagnetic metals considered most useful for MRI studies, for example trivalent gadolinium. Toxicity of trivalent gadolinium has been reduced by combining it with dimethyltetraaminopenta-acidic acid to form complex that exhibits less toxicity than the gadolinium salt. However, some studies with gadolinium DTPA indicate problems similar to those encountered with super paramagnetic iron oxide such as side effects of diarrhea and meteorism. In addition, the toxicity of the complex has not been fully determined. Toxicity has not been observed with the use of zeolite-enclosed gadolinium This may be due to relatively tight binding of the metal ion within the zeolite.

Although the invention has been illustrated with trivalent gadolinium and divalent manganese, other ion species that ion exchange with a zeolite could be used. Examples include tetravalent vanadium, trivalent vanadium, divalent copper, divalent nickel, trivalent chromium, divalent cobalt, divalent iron, trivalent iron and trivalent cobalt. Any of a variety of salts of these species may be used, including chlorides, acetates, nitrates and the like. These examples are not intended to be limiting and other species capable of ion exchanging include members of the lanthanide series of elements and the rare earth elements.

There are numerous zeolites that can be used for the entrapment of paramagnetic ions and are therefore useful for the practice of the invention. For example, the synthetic zeolites type A, type X, type Y or ZSM-5 zeolite are particularly useful (5,6). There are many types of zeolites, differing in chemical composition, cavity diameter or natural occurrence, such as the mordenite class of zeolites. Shapes of these substances are to some extent derived from the linkages of secondary building units forming the typical three-dimensional framework of the molecules. The shapes may then have an effect on ion exchange ability, selectivity in restricting the passage of molecules based on size, and absorption properties.

Materials similar to zeolites may be used to enclose metal ions useful for imaging. Molecular sieves, for example, are structurally similar to zeolites. Zeolite building blocks are $Si^{+4}$ and $Al^{+4}$ tetrahedra linked through common oxygen atoms extending in an infinite 3-dimensional network. When isomorphic atoms are substituted for aluminum or silicon (e.g., gallium, germanium or phosphorus) synthetic zeolites, more commonly known as molecular sieves are created. Use of molecular sieves that possess ion exchange properties may be used analogously to zeolites.

Ion exchange properties of the zeolite are particularly important in preferential binding of certain ions, particularly metal ions of the transition metal series. The amount of metal ion actually enclosed within the zeolite will depend on the characteristics of the particular zeolite type used, as well as the presence of other positively charged ions. Thus, for example, if calcium zeolite type A is mixed with a gadolinium salt and allowed to equilibrate over a period of time, the final exchange product will contain both positively charged gadolinium and calcium ions. It has been found that these zeolites, however, will preferentially exchange with the transition metal series so that there are greater concentrations of the transition metal ions than the ions from group 1 or group 2 elements. At any rate, the preferential binding of paramagnetic ions such as $Gd^{+3}$ and $Mn^{+2}$ is sufficient to give excellent MRI imaging properties when the paramagnetic zeolite entrapped ion is used for imaging studies.

Zeolite enclosed paramagnetic ions are particularly useful for MRI studies of the gastrointestinal tract, especially since pharmaceutically acceptable preparations of these materials can be administered enterically, for example, by nasogastric tube to either an animal or a human being. Oral administration is preferred for most applications involving studies or treatment of humans.

Detection of the zeolite enclosed paramagnetic ion after administration is most preferably performed by magnetic resonance imaging, although conventional radiographic imaging and CT may also be employed similar to methods used with $BaSO_4$ and gastrographin imaging. High Z (atomic weight) metals like gadolinium may also be detected by monochromatic x-ray sources, for example, K-edge imaging.

In a most preferred method of practice, the invention is used for gastrointestinal tract imaging. A pharmaceutically acceptable formulation including zeolite enclosed trivalent gadolinium is administered, preferably orally, to a human or animal and detected by magnetic resonance imaging. The trivalent gadolinium may be enclosed within calcium type A zeolite or sodium type X zeolite or any other suitable zeolite. The zeolite is prepared in a pharmaceutical carrier.

The zeolite enclosed metal ion compounds of this invention may be combined with pharmaceutically acceptable formulating agents, dispersing agents and fillers. Powders, granules, capsules, coated tablets, syrupy preparations and aqueous suspensions may be utilized for oral preparations. Formulating agents employed may be either solid or liquid, including but not limited to such solids as calcium phosphate, calcium carbonate, dextrose, sucrose, dextrin, sucrose ester, starch, sorbitol, mannitol, crystalline cellulose, talc, kaolin, synthetic aluminum silicate, carboxymethyl cellulose, methylcellulose, cellulose acetate phthalate, alginates, polyvinyl pyrrolidone, polyvinyl alcohol, gum arabic, tragacanth gum, gelatin, bentonite, agar powder, shellac, Tween 80, carrageenans and psyllium. Modified zeolite materials having residual charges or modifying groups might also be used which may be adsorbed to various carrier matrices such as clay. Examples of liquids suitable as suspending fluids include water, isotonic salt solution, ethanol, propylene glycol, polyethylene glycol, glycerol, Hartman's solution and Ringer's solution. A preferred liquid for suspension is EZpaque supernatant which is readily obtained from EZpaque after removing $BaSO_4$, either by centrifugation or filtration.

Administration is most preferably oral because of better patient acceptance in that form but administration may also be enteric, vaginal, anal or by direct introduction into the gastrointestinal tract at any point such as by introduction through tubes accessing the alimentary canal. Examples of nonoral use include retrograde pelvic studies and investigations to define vaginal contents. Flavor enhancers may be added to oral preparations, including taste masking substances such as sweeteners and citrus flavors. Other additives, including color, preservatives, bulk or antifoam agents may also be included in the formulation.

The invention may also be used in conjunction with magnetic resonance imaging of body surfaces. For example, artificial limbs must be custom fitted to leg, arm, hand or foot amputees. Present methods are time-consuming and rendered difficult because photographs show only skin surface while x-ray indicates only dense material such as bone. MRI could show both bone and skin and therefore facilitate design of a prosthetic device which must be customized to the remaining member of the body. Zeoliteenclosed trivalent gadolinium would be ideal for this purpose. The crystalline material would be powdered sufficiently to be conveniently applied to a skin surface, preferably as an aerosol which could be either a dry powder or a suspension in a suitable fluid, for example water or alcohol. The skin is preferably first treated with an agent that promotes adherence of the powder to the surface, for example, tincture of benzoin. Other applications envisioned are imaging of the foot, useful in customizing footwear for abnormal or injured feet. Surface imaging could also be used in connection with inanimate surfaces, for example some metal surfaces. In some cases, especially where high resolution was desired, uniform application would be important so that surface roughness reflected the surface examined rather than an artifact of uneven application.

The invention may also be used to evaluate lung ventilation. An aerosol of suitably small particles, in the nanometer range, would be inhaled by the patient prior to MRI scans to determine lung ventilation.

The zeolite enclosed ionic species of this invention will typically be formulated as suspensions or dispersions, preferably in EZ dispersant (available from E-ZM Company) or used as the supernatant from pharmacy-purchased suspensions of $BaSO_4$ under the trade name of EZpaque) at a low weight to volume ratio. For oral administration this is preferably approximately 1%. Higher concentrations of the zeolite composition may be prepared as suspensions; however, for MR imaging purposes, image intensity decreases markedly above weight ratios of 1%. The 1% suspensions in EZpaque supernatant appear to be stable indefinitely.

A marked advantage of calcium gadolinium enclosed in type A zeolite is the relatively low concentration that may be employed in a dispersing medium. For example, a one percent concentration of calcium gadolinium type A zeolite administered orally is effective in producing excellent images for MRI studies, although higher weight percent concentrations may be utilized in accordance with the form of the preparation. In contrast, when barium sulfate is used in the same dispersing medium, concentrations of up to 40-50% by weight are required and precipitation is often a problem.

A most preferred paramagnetic ion useful for GI studies of this sort is trivalent gadolinium, however, other metal ions as listed above can be used. Excellent results have also been obtained using zeolite enclosed divalent manganese.

It will be appreciated by those of skill in the art that there will always be present within the zeolite not only the paramagnetic ion which is used for the imaging, but also a second ion with which the paramagnetic ion was exchanged. The type of second ion will depend on the zeolite compound used in the preparation. For example, calcium zeolite, calcium type A zeolite, sodium zeolite or other salts formed from first and second group elements may be used. Alternatively, the parent zeolite could be exchanged with protons, alkali or alkaline earth metal ions, transition or rare earth metal ions prior or subsequent to entrapment of a paramagnetic ion. It should be further understood that a zeolite enclosing a paramagnetic ion may contain other ligands such as hydroxyl ion, chloride ion or water depending on the method of preparation. Any or all of these species may affect the properties of the enclosed ions. The presence of any one or a number of these may alter or attenuate the pharmacological effects of the zeolite enclosed paramagnetic ion.

DETAILED DESCRIPTION OF PREFERRED EMBODIMENTS

The following examples illustrate preferred embodiments of the practice of the invention. It should be understood that these examples are intended to be illustrative of the invention and in no way limiting.

EXAMPLE 1

Preparation of Zeolite-enclosed Trivalent Gadolinium

Calcium zeolite (calcium A), 10 g, was mixed with 2 g of $GdCl_3 \cdot 6H_2O$ in approximately 100 ml deionized water and stirred at 30° C. for 18 hr. The resulting zeolite suspension was suction filtered and washed extensively with deionized water until negative for chloride ion by silver nitrate test. The resulting CaGdA gave a negative test for free $Gd^{+3}$ using the colorimetric indicator, xylenol orange. The zeolite was dried in a vacuum oven overnight at 50° C. The resulting sample contained 3.24% trivalent gadolinium by weight. Analogous procedures using NaA, NaX or NaY yielded the percent weight compositions shown in Table 1. $MnCl_2$ used in place of $GdCl_3$ formed MnNaX when exchanged into NaX.

TABLE 1

| Compound | Weight percent metal |
|---|---|
| GdNaA | 6.18 |
| GdCaA | 3.24 |
| GdNaX | 6.19 |
| GdNaY | 3.11 |
| MnNaX | 5.59 |

Various zeolites were suspended in EZ dispersant at the indicated weight percent and image intensity data recorded as shown in Table 2.

TABLE 2

| Compound | Intensity[1] | Std. Deviation | % sol'n* |
|---|---|---|---|
| GdNaY | 1061.43 | 29.76 | 1 |
|  | 382.19 | 12.42 | 0.1 |

TABLE 2-continued

| Compound | Intensity[1] | Std. Deviation | % sol'n* |
|---|---|---|---|
| | 259.49 | 8.45 | 0.01 |
| | 228.97 | 8.55 | 0.001 |
| | 187.65 | 7.67 | 0.0001 |
| GdNaX | 454.08 | 19.91 | 1 |
| | 1273.13 | 36.84 | 0.1 |
| | 349.54 | 13.93 | 0.01 |
| | 219.17 | 10.84 | 0.001 |
| | 64.49 | 10.77 | 0.0001 |
| GdNaA | 365.06 | 12.51 | 1 |
| | 1522.71 | 29.67 | 0.1 |
| | 391.05 | 8.90 | 0.01 |
| | 237.03 | 9.37 | 0.001 |
| | 193.79 | 8.39 | 0.0001 |
| GdCaA | 408.25 | 47.06 | 1 |
| | 772.24 | 27.09 | 0.1 |
| | 280.11 | 10.38 | 0.01 |
| | 230.06 | 7.69 | 0.001 |
| | 200.32 | 8.56 | 0.0001 |
| MnNaX | 34.57 | 6.50 | 1 |
| | 1312.48 | 29.02 | 0.1 |
| | 453.10 | 16.17 | 0.01 |
| | 257.36 | 6.90 | 0.001 |
| | 185.37 | 8.66 | 0.0001 |

[1] Mean value
*All sample zeolites suspended in EZpaque supernatant at the indicated wt %.

EXAMPLE 2

Figure 1A:
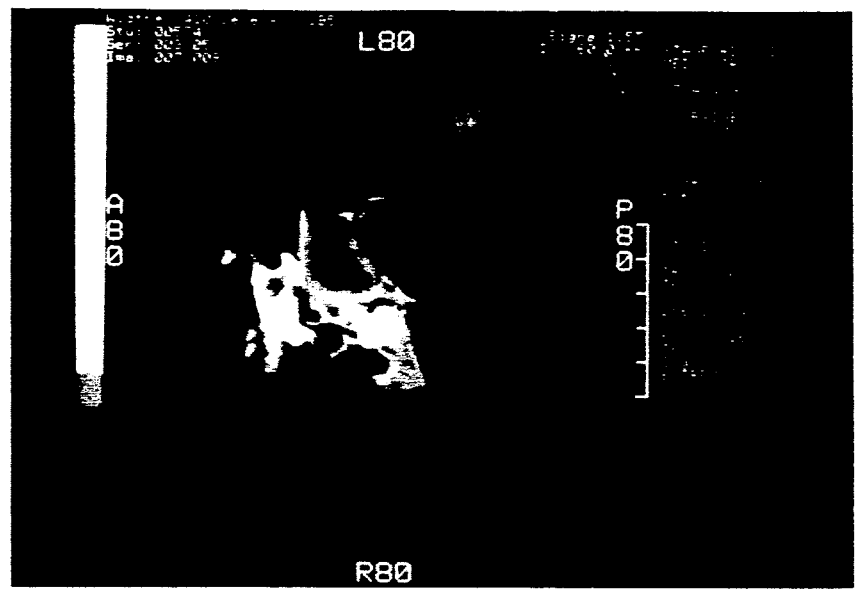
FIG. 1 is an MRI scan of the gastrointestinal tract of a rabbit taken after two administrations by NG tube of a 1% suspension of CaGdA at 12 hr and 4 hr before MRI scanning. Panel IA illustrates the effect of the presence of CaGdA in the stomach. Panel 1B indicates delineation of the jejunum region of the intestine in the presence of CaGdA.
Figure 1B:
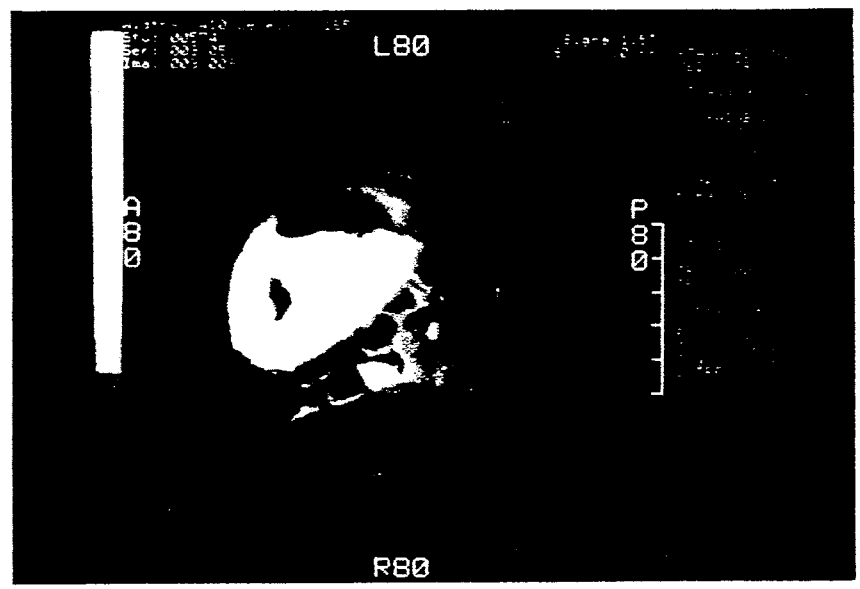

Gastrointestinal Imaging in the Rabbit 1 g of CaGdA was suspended in 99 ml dispersing medium prepared from E-Zpaque ™ supernatant obtained by centrifugation of the $BaSO_4$. Approximately 200-300 cc was introduced into the stomach of a rabbit using a pediatric nasogastric (NG) tube at 12 hr and 4 hr prior to MRI. MRI scans were obtained periodically using a conventional $T_1$ weighed sequence. FIG. 1 is an MRI scan 4 hr after the last administration. CaGdA was detected in the stomach, as indicated by the bright region in Panel A. 12 hr after administration the majority of the CaGdA had passed into the intestine and, as shown in Panel B, was concentrated in the jejunum region.

EXAMPLE 3

Gastrointestinal Imaging in the Dog

Figure 2A:
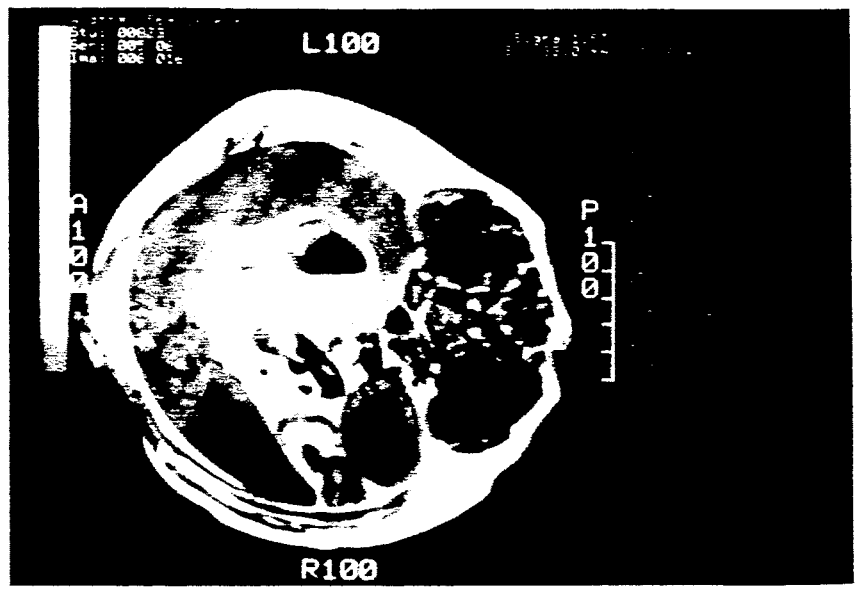
FIG. 2 is an MRI scan of the gastrointestinal tract of a dog taken after administration by NG tube of a 1% suspension of CaGdA. Panels A and B are scans taken 1 hr after administration. Panels C and D are scans taken 3 hr after administration.
Figure 2B:
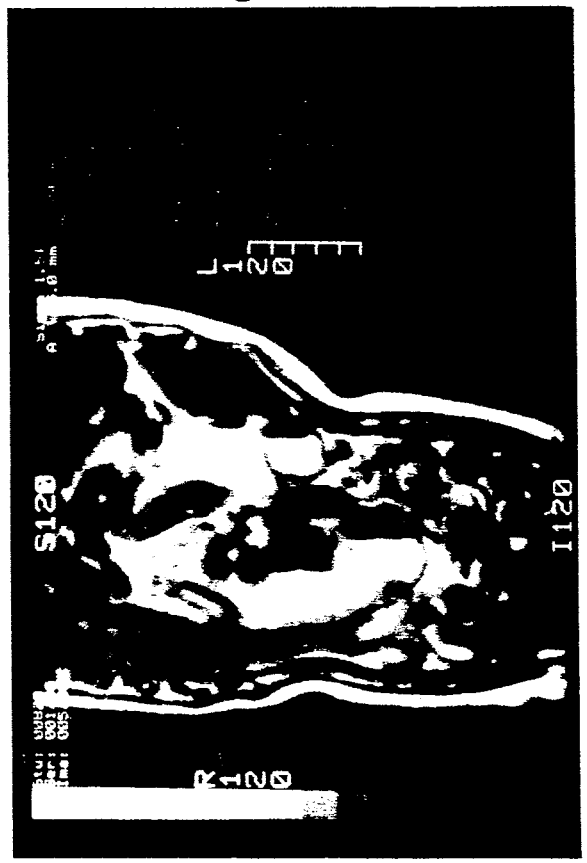
Figure 2C:
Figure 2D:

Experimental protocol as described in Example 2 was followed in imaging the gastrointestinal tract of a dog, except that approximately 500 cc of 1% suspension of CaGdA was administered via NG tube. FIG. 2A is an MRI scan taken 1 hour after administration. FIG. 2B is an MRI scan taken 3 hours after administration.

PROPHETIC EXAMPLE 4

The present example outlines the procedure contemplated by the Applicants to be useful for the successful imaging of fistulas.

MRI Fistulagrams

A human patient will have been diagnosed as having a fistula. Generally, indications of infection should not be present as injection of fluid into the fistula might cause delocalization of an infection. In appropriate cases, the fistula will be injected with a suspension of 1% GdNaX in a suitable vehicle such as EZpaque supernatant. 5-15 cc injections will be used, depending on the size of the fistula. Imaging will then be performed using standard MRI procedures in order to visualize extent and location of fistulous tracts.

PROPHETIC EXAMPLE 5

The present example outlines the procedure contemplated by the Applicants to be useful for the successful imaging of the gastrointestinal tract in pediatric practice.

MRI Imaging in Pediatric Patients

Young patients generally do not tolerate hyperosmolic iodinated agents currently in use. The following procedure would be used in this group of patients. The patient is administered 100-150 cc of a 1% solution of GdNaX in EZpaque supernatant or other suitable vehicle via a pediatric NG tube. The administered suspension must not be hyperosmolar. Images are obtained immediately after administration using standard MRI imaging procedures.

PROPHETIC EXAMPLE 6

The present example outlines the procedure contemplated by the Applicants to be useful for the successful imaging of surfaces to which prosthetic devices are to be fitted.

MRI of Amputated Human Long Limb Members

The limb to which a prosthetic device is to be fitted is prepared for attachment of a prosthetic device by surgical procedures as medically indicated to provide a suitable attachment surface. The surface is then coated with a material such as benzoin that will facilitate adherence of an applied powder to the surface. Zeolite-enclosed gadolinium, prepared as described in Example 1, is sufficiently to allow easy dispersion in a liquid or as an aerosol, washed extensively in water until the wash is free of gadolinium as determined by testing with xylenol orange, and then applied to the skin surface. Application is with an aerosol, either as a dry powder or as a suspension in a suspending agent such as alcohol or water. After the surface is coated with a fine layer of powder, images are obtained by standard magnetic imaging procedures. The resulting images are used to design custom matings for the artificial limb.

PROPHETIC EXAMPLE 7

The present example outlines the procedure contemplated by the Applicants to be useful for the successful imaging of the lungs in evaluating lung ventilation.

Lung Ventilation Evaluation

Zeolite-enclosed gadolinium is prepared as described in Example 1. After drying, the solid is ground to approximately nanometer range. From this an aerosol in a compatible inhalant is prepared. The aerosol is administered and imaging performed using standard MRI imaging procedures.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, any of a number of zeolites or molecular sieves could be used as the enclosing matrix and any of a number of cationic species could be present within the zeolite, some of which could be used to modify effects of the enclosed ion of interest, for example, trivalent gadolinium in imaging studies. These and obvious related modifications are contemplated to be within the scope of the claims.

REFERENCES

The references listed below are incorporated herein by reference to the extent they supplement, explain, provide a background for or teach methodology, techniques and/or compositions employed herein.

1. Lönnemark, M., Hemmingsson, A., Bach-Gansmo, T., Ericsson, A., Öksendal, A. Nyman. R. and Moxnes, A., Acta Radiol. 30, 193-196 (1989).
2. Hahn, P.F., Staark, D.D., Lewis, J.M., Saini, S., Elizondo, G., Weissleder, R., Fretz, C.J. and Ferrucci, J.T., Radiology 175, 695-700 (1990).
3. Claussen, Von C., Kornmesser, W., Laniado, M., Kaminsky, S., Hamm, B. and Felix, R., ROFO 148, 683-689 (1989).
4. Braybrook, H.H. and Hall, L.D., Drug. Des. Deliv. 4, 93-95 (1989).
5. Breck, D.W., *Zeolite Molecular Sieves*, Krieger Publishing Company, Malabar, FL, 1984.
6. Rankel, L.A. and Valyocaik, E.W., U.S. Pat. No. 4,388,285, Jun. 14, 1983.

What is claimed is:

1. An imaging method comprising administering to an animal an amount of zeolite-enclosed paramagnetic ion, said amount being effective as a contrast or image-brightening agent.
2. The method of claim 1 wherein the animal is a human.
3. The method of claim 1 wherein the paramagnetic ion comprises a rare earth element.
4. The method of claim 1 wherein the paramagnetic ion comprises a transition metal ion.
5. The method of claim 1 wherein the paramagnetic ion comprises $V^{+4}$, $Cu^{+2}$, $V^{+3}$, $Ni^{+2}$, $Cr^{+3}$, $Co^{+2}$, $Fe^{+2}$, $Co^{+3}$, $Mn^{+2}$ or $Fe^{+3}$.
6. The method of claim 1 wherein the zeolite is characterized as having ion exchange properties sufficient to facilitate preferential binding of the paramagnetic ion.
7. The method of claim 1 wherein the zeolite comprises type A, type X, type Y or ZSM-5 zeolite.
8. The method of claim 1 wherein the zeolite comprises mordenite type zeolite.
9. The method of claim 1 wherein the zeolite enclosed paramagnetic ion is administered anally, vaginally or by direct injection into a fistulous region.
10. The method of claim 1 wherein the zeolite enclosed paramagnetic ion is administered enterically.
11. The method of claim 1 wherein the zeolite enclosed paramagnetic ion is administered orally.
12. The method of claim 1 wherein the contrast or imagebrightening agent is detected by magnetic resonance.
13. A method for gastrointestinal tract imaging comprising orally administering a pharmaceutically acceptable formulation comprising zeolite enclosed trivalent gadolinium and detecting the gadolinium by magnetic resonance imaging.
14. The method of claim 12 wherein the zeolite-enclosed trivalent gadolinium is CaGdA or NaGdX.
15. A method for gastrointestinal tract imaging comprising orally administering a pharmaceutically acceptable formulation comprising zeolite enclosed divalent manganese and detecting the manganese by magnetic resonance imaging.
16. The method of claim 15 wherein the zeolite-enclosed divalent manganese is CaMnA or NaMnX.
17. A pharmaceutical composition comprising a zeolite-enclosed paramagnetic ion and a pharmaceutically acceptable carrier selected from the group consisting of a non-aqueous suspending liquid, a powder or an absorbing matrix.
18. The pharmaceutical composition of claim 17 wherein the pharmaceutically acceptable carrier is an oral preparation.
19. The pharmaceutical composition of claim 17 wherein the zeolite-enclosed paramagnetic ion is a transition metal ion.
20. The pharmaceutical composition of claim 17 wherein the paramagnetic ion comprises trivalent gadolinium.
21. The pharmaceutical composition of claim 17 wherein the paramagnetic ion comprises $Mn^{+2}$.
22. The pharmaceutical composition of claim 17 wherein the zeolite has ion exchange capacity sufficient to preferentially exchange the paramagnetic ion.
23. The pharmaceutical composition of claim 17 further comprising an amount of a second ion sufficient to alter or attenuate pharmacological effects of said zeolite-enclosed paramagnetic ion.
24. The pharmaceutical composition of claim 23 wherein the second ion is a metal ion or a metal ion complex.
25. The composition of claim 23 wherein the second metal ion is $Na^{+1}$ or $Ca^{+2}$.
26. The composition of claim 23 wherein the second ion is a nonmetal cationic species.
27. The composition of claim 23 wherein the second ion is $H^+$, $NH_4^+$ or $R_4N^+$ wherein R is an alkyl group or hydrogen selected in combination to prepare a cationic species enclosable by the zeolite.

* * * * *